(12) United States Patent
Takada et al.

(10) Patent No.: US 7,101,072 B2
(45) Date of Patent: Sep. 5, 2006

(54) PHOTOIRRADIATION DEVICE AND FIBER ROD

(75) Inventors: Mitsuaki Takada, Tokyo (JP); Aiichi Kobayashi, Tokyo (JP); Shinya Omori, Tokyo (JP); Masafumi Ohno, Tokyo (JP)

(73) Assignees: GC Corporation, Tokyo (JP); Stanley Electric Co., Ltd., Tokyo (JP)

( * ) Notice: Subject to any disclaimer, the term of this patent is extended or adjusted under 35 U.S.C. 154(b) by 212 days.

(21) Appl. No.: 10/792,617

(22) Filed: Mar. 3, 2004

(65) Prior Publication Data

US 2004/0228142 A1 Nov. 18, 2004

(30) Foreign Application Priority Data

Mar. 13, 2003 (JP) .............................. 2003-068188
Mar. 13, 2003 (JP) .............................. 2003-068194

(51) Int. Cl.
*A61B 1/07* (2006.01)
*A61B 1/06* (2006.01)

(52) U.S. Cl. ...................... 362/573; 362/800; 362/804; 362/235; 362/240; 385/93; 385/119; 433/29

(58) Field of Classification Search ........ 362/572–574, 362/611–613, 621, 240, 804
See application file for complete search history.

(56) References Cited

U.S. PATENT DOCUMENTS

| 4,483,585 A | 11/1984 | Takami | 385/115 |
| 5,412,750 A | 5/1995 | Nath | 385/125 |
| 5,513,291 A * | 4/1996 | Buchin et al. | 385/93 |
| 6,200,134 B1 | 3/2001 | Kovac et al. | 433/29 |
| 6,419,483 B1 * | 7/2002 | Adam et al. | 433/29 |
| 6,955,537 B1 * | 10/2005 | Cao | 433/29 |

FOREIGN PATENT DOCUMENTS

WO    WO 0067660    11/2000

OTHER PUBLICATIONS

European Patent Office, Patent Abstracts of Japan, vol. 1996, No. 10, Oct. 31, 1996 (of JP 08 141001 A published Jun. 4, 1996).

* cited by examiner

*Primary Examiner*—Alan Cariaso
*Assistant Examiner*—Leah Lovell
(74) *Attorney, Agent, or Firm*—Ladas & Parry LLP

(57) ABSTRACT

A photoirradiation device in which an optical system can be miniaturized and utilization efficiency of light can be improved in a manner that includes a first lens and a second lens, which share refraction of light to convert light beams emitted from a plurality of light sources into the light beams substantially parallel to an optical axis, and a third lens focusing the light beams from the second lens on an incident surface 20A of a lightguide 20. A fiber rod which can output uniform light beams in a manner that includes a first rod having a single fiber and a second rod having a plurality of fibers.

7 Claims, 7 Drawing Sheets

(A)

(B)

PHOTOIRRADIATION DEVICE AND FIBER ROD

FIELD OF THE INVENTION

The present invention relates to a photoirradiation device which focuses light beams emitted from a plurality of point light sources to irradiate. Further, the invention relates to a fiber rod and the photoirradiation device which uses the fiber rod.

DESCRIPTION OF THE RELATED ART

A photo-polymerization resin becomes widespread as a dental material for restoration of tooth in dentistry. The photo-polymerization resin is filled into a cavity of a tooth of a patient, and then the photo-polymerization resin is cured by being irradiated with light from the photoirradiation device. The photoirradiation devices including a plurality of light-emitting diodes as well as the photoirradiation devices in which a halogen lamp or a xenon lamp is used as the light source are well known.

In Japanese Patent No. 2979522 (FIGS. 1 to 3), there is disclosed a device which includes the plurality of light-emitting diodes and focuses the light beams emitted from the light-emitting diodes to output the focused light beams. More specifically, there are some modes such as the photoirradiation device in which individual light-emitting diode and an irradiation opening are connected through an optical fiber, the photoirradiation device in which the irradiation light beam emitted from each light-emitting diode is guided to an incident port of a photoirradiation head through one condenser lens, and the photoirradiation device in which the irradiation light beam emitted from each light-emitting diode is guided to the incident port of the photoirradiation head by reflecting the irradiation light with a reflecting mirror.

However, in the photoirradiation device in which individual light-emitting diode and the irradiation opening are connected through the optical fiber, when a distance between an end face of the optical fiber and the light-emitting diode becomes longer, there was a problem that utilization efficiency of the light is decreased and high accuracy is required for positioning.

In the photoirradiation device in which the irradiation light beam emitted from each light-emitting diode is guided to the incident port of the photoirradiation head through one condenser lens, there was the problem that it is difficult to focus the irradiation light beam of the light-emitting diode arranged at a position which is far away from an optical axis and the utilization efficiency of the light is decreased. Further, in the photoirradiation device using the reflecting mirror, there was the problem that the device is enlarged.

In order to avoid these problems, it is considered that the light-emitting diodes are arranged as dense as possible. However, heat dissipation becomes the problem in such the arrangement. That is to say, when light output is increased, the number of light-emitting diodes is increased and it is difficult to cool efficiently the heat generation. Additionally, the light output is decreased by the heat generation.

In view of the foregoing, it is an object of the first invention to provide a photoirradiation device which has a small size and the high utilization efficiency of the light beam.

In Japanese Patent No. 2979522 (FIG. 2), there is disclosed the device which includes the plurality of light-emitting diodes and focuses the light beams emitted from the light-emitting diodes to output the light beams through the optical fiber.

In the optical fiber, there are a clad rod type optical fiber which includes one fiber, and a fiber array type optical fiber in which the plurality of fibers are bundled. In the clad rod type optical fiber, when the fiber is bent, the incident light beam is irregularly reflected to increase a damping factor.

In the dental photoirradiation device, since it is necessary that a front end of the photoirradiation device is inserted into the oral cavity of the patient to irradiate the tooth with the light, a part of the optical fiber is often bent. Therefore, usually the fiber array type optical fiber is adopted for the optical fiber in the photoirradiation device.

However, when the light beams emitted from such the plurality of point light sources as plurality of light-emitting diodes are guided using the fiber array type optical fiber, the irradiation light beams are affected by a light beam distribution at an incident light unit 20A. FIG. 8 is an explanatory view showing a state in which the light beams emitted from the plurality of light-emitting diodes are outputted through the fiber array type optical fiber. As shown in FIG. 8, the irradiation light beams are divided into a plurality of spot lights S1, S2, . . . .

Therefore, the subject to be irradiated is not uniformly irradiated with the light, and a region which is irradiated with the light and the region which is not the irradiated with the light are generated. In the dental photoirradiation device, since the photo-polymerization resin is cured by irradiating the photo-polymerization resin with the light, when the fiber array type optical fiber is used, there is generated the problem that the cured region and the uncured region are generated in the photo-polymerization resin and the photo-polymerization resin can not be uniformly cured.

In view of the foregoing, it is an object of the second invention to provide a fiber rod, which can guide the light beams emitted from the plurality of point light sources with low damping factor and uniform the irradiation light beams, and a photoirradiation device using the fiber rod.

SUMMARY OF THE INVENTION

Some aspects for solving the problems of the invention will be described below. Although reference numerals of the accompanying drawings are added with a parenthesis in order to simplify understanding of the invention, the invention is not limited to the modes shown in the accompanying drawings.

A photoirradiation device (100) according to the first invention which outputs a light beam from an outgoing surface (20B) of a lightguide unit (20), the photoirradiation device (100) comprising a plurality of point light sources (D1 to D8), the lightguide unit (20) which has an incident surface (20A) and the outgoing surface (20B), the lightguide unit (20) guiding the light beam incident to the incident surface (20A) to the outgoing surface (20B), and an optical system which focuses the light beams emitted from the plurality of point light sources (D1 to D8) on the incident surface (20A) of the lightguide unit (20), wherein the plurality of point light sources (D1 to D8) are arranged on a surface perpendicular to an optical axis of the optical system, the optical system has a first lens (111), a second lens (12), and a third lens (13), which are arranged in order from the point light sources (D1 to D8) toward the incident surface (20A) of the lightguide unit (20), an incident surfaces and an outgoing surfaces in the first lens (111) and the second lens (12) are formed so that the light beam emitted from the point light source arranged near the optical axis is converted into the light beam substantially parallel to the optical axis, and an incident surface and an outgoing surface of the third lens (13) are formed so that the light beams outgoing from the second lens (12) are focused on the incident surface (20A) of the lightguide unit (20), while the light beam has an incident angle which can be incident to the lightguide unit (20) in consideration of a numerical aperture (NA) of the lightguide unit (20).

When the light beams emitted from the plurality of point light sources are converted into the light beams parallel to the optical axis by using only one lens, the number of light beams internally reflected at the outgoing surface of the lens is increased, and the utilization efficiency of the light beam is decreased. According to the invention, since the light beams emitted from the point light sources are converted into the light beams parallel to the optical axis by using the first lens and the second lens, refraction of the light beams can be shared by the first lens and the second lens. As a result, a curvature of the outgoing surface of the first lens can be decreased to prevent the internal reflection, and the light beams emitted from the plurality of point light sources can be efficiently utilized. Accordingly, since larger output can be obtained with the small number of point light sources, the optical system can be miniaturized, which in turn allows the overall size of the device to be miniaturized.

It is preferable that the incident surface of the first lens (111) has a flat surface or a convex surface and the outgoing surface of the first lens (111) has the convex surface. In particular, when the incident surface of the first lens (111) is formed to be flat, productivity can be improved. It is also appreciated that the outgoing surface of the first lens (111) has an aspheric surface. Accordingly, a large refractive index can be obtained.

It is preferable that the incident surface of the second lens (12) has the flat surface or a concave surface and the outgoing surface of the second lens (12) has the convex surface. When the outgoing surface of the second lens and the incident surface of the third lens have the spherical surface, the spherical aberration is generated. Therefore, among the light beams passing through outer peripheral portion far away from the optical axis, the number of light beams which do not impinge on the incident surface of the lightguide unit and the number of light beams whose incident angles exceed an angle at which the light beam can be incident are increased by the spherical aberration. By forming the incident surface of the second lens in the concave shape, the spherical aberration can be decreased and light quantity incident to the incident surface of the lightguide unit can be increased. In other words, it is preferable to define the incident surface of the second lens so that the spherical aberration generated in the outgoing surface of the second lens and the incident surface of the third lens is corrected.

It is preferable that the incident surface of the third lens (13) has the convex surface and the outgoing surface of the third lens (13) has the flat surface. It is preferable that the plurality of point light sources (D1 to D8) are arranged at a position which is inside a primary focus of the optical system (near the first lens 111), and the incident surface (20A) of the lightguide unit (20) is arranged at a secondary focus of the optical system. Accordingly, the light beams emitted from the plurality of point light sources can be efficiently incident to the lightguide unit.

Further, it is preferable that the point light sources (D1 to D8) area light-emitting diode. The light-emitting diodes having the same peak wavelengths in which emission quantity becomes a maximum, or the light-emitting diodes having the peak wavelengths different from one another may be used.

A fiber rod (20) according to the second invention (hereinafter also referred to as "lightguide" or "lightguide unit") which guides a light beam incident to an incident surface (20A) to output the light beam from an outgoing surface (20B) by using a fiber including a high-refractive index core (C1) and a low-refractive index clad (C2) covering the core, the fiber rod comprising a first rod (21) which has a single fiber whose one end becomes the incident surface (20A), and a second rod (22) which has the plurality of fibers, the second rod (22) taking the light beam outgoing from another end of the first rod (21) from one end of the second rod (22) and outputting the light beam from the other end which becomes the outgoing surface (20B).

According to the invention, the clad rod type of first rod is provided on the incident side and the fiber array type of second rod is provided on the outgoing side. Since the clad rod type of first rod guides the incident light beam to the second rod while the incident light beam is diffused, the light beam outgoing from the outgoing surface can have the spread. Accordingly, even if the incident light beams are the light beams from the plurality of point light sources, the uniform irradiation light can be obtained without dividing the irradiation light into the plurality of spot lights.

It is preferable that the first rod (21) has a linear shape and the second rod (22) has a bent portion (23). Since it is difficult in the fiber array type of second rod to increase a damping factor caused by the curvature compared with the clad rod type of first rod, the incident light beam can be guided with low damping factor by providing the curvature in the second rod.

A photoirradiation device according to the invention comprising a plurality of light-emitting diodes (D1 to D8), the above fiber rod (20), and an optical system (111, 12, 13) focusing light beams emitted from the plurality of light-emitting diodes on the incident surface (20A). In this case, it is preferable that the incident surface is arranged near one of focal points of the optical system.

According to the invention, the light beams emitted from the plurality of point light source scan be guided with low damping factor and the irradiation light beam can become uniform.

DETAILED DESCRIPTION OF THE INVENTION (First Invention)

An embodiment of the first invention will be described below referring to the accompanying drawings. In the embodiment, the dental photoirradiation device for curing the photo-polymerization resin will be described as an example of the photoirradiation device.

Figure 1:
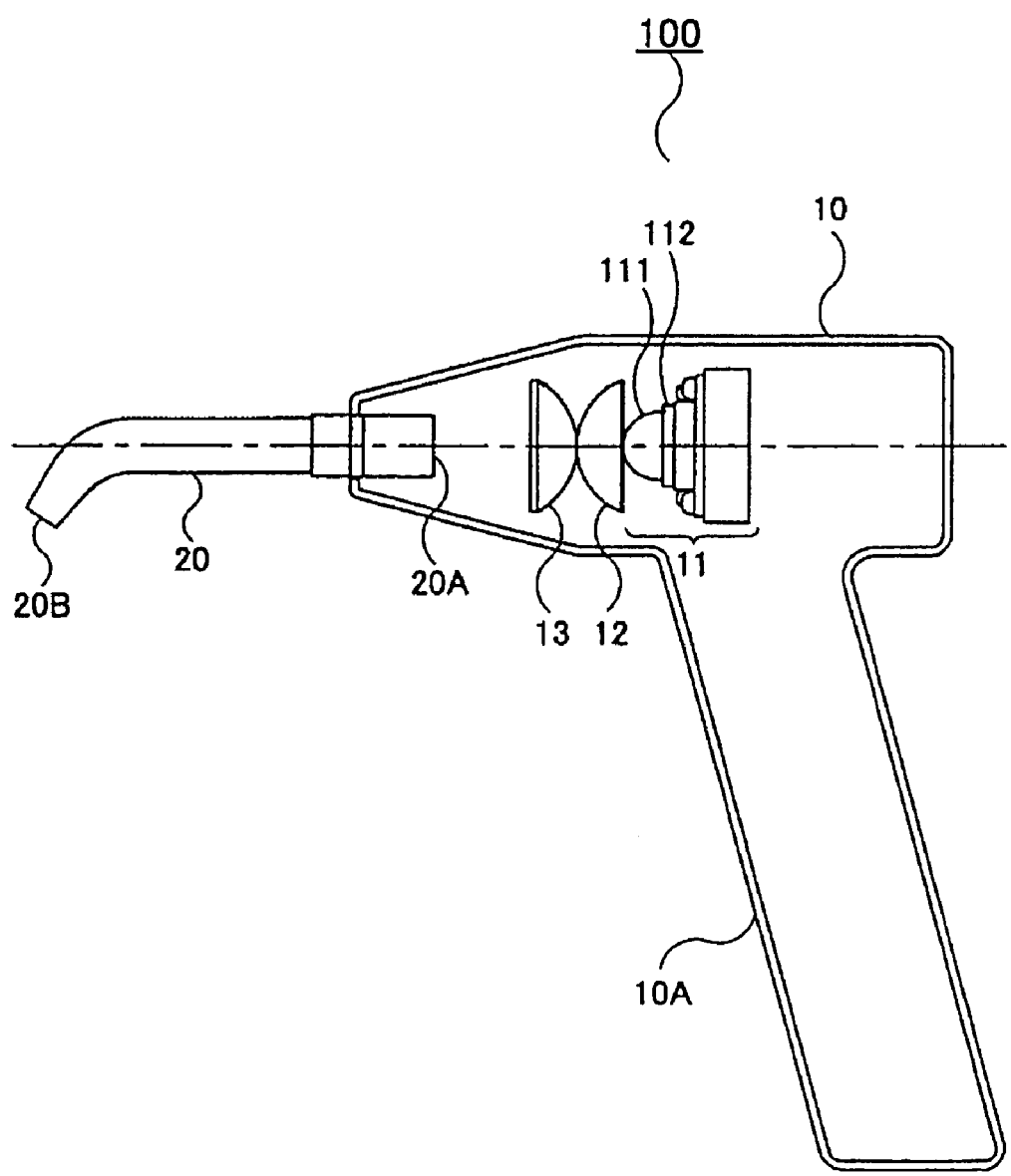
FIG. 1 is a sectional view showing a mechanical configuration of a dental photoirradiation device according to an embodiment of the invention.

FIG. 1 is a sectional view showing a configuration of the dental photoirradiation device according to the embodiment. A dental photoirradiation device 100 includes a main body 10 and a lightguide 20 which is provided on an end of the main body 10. The main body 10 has a cannonball shape, a pencil shape, or the like. Sometimes a grip 10A is provided in the main body as shown in FIG. 1. A control switch or the like (not shown) is provided in the main body 10 or the grip 10A, so that a dentist can operate to turn on and off the irradiation while holding the main body 10 or the grip 10A.

The main body 10 incorporates an LED light-emitting unit 11, a second lens 12, and a third lens 13. The LED light-emitting unit 11 includes a first lens 111 and an LED package 112 in which a plurality of light-emitting diodes are arranged. The light-emitting diodes arranged in the LED package 112 function as the point light source.

In the lightguide (fiber rod) 20, a glass optical fibers, a plastic optical fibers, or the like, which has low optical transmission loss, are integrally bundled. As shown in FIG. 1, it is preferable that a front end side of the lightguide 20 is slightly bent in order to irradiate easily the photo-polymerization resin which is filled into a cavity of a tooth. The lightguide 20 functions as the lightguide unit which outputs the light beam incident to an incident surface 20A from an outgoing surface 20B.

In the dental photoirradiation device 100, the light beams emitted from the plurality of light-emitting diodes are focused on the incident surface 20A of the lightguide 20 with an optical system including the first lens 111, the second lens 12, and the third lens 13. Then, the light beams are outputted from the outgoing surface 20B through the lightguide 20.

Figure 2:
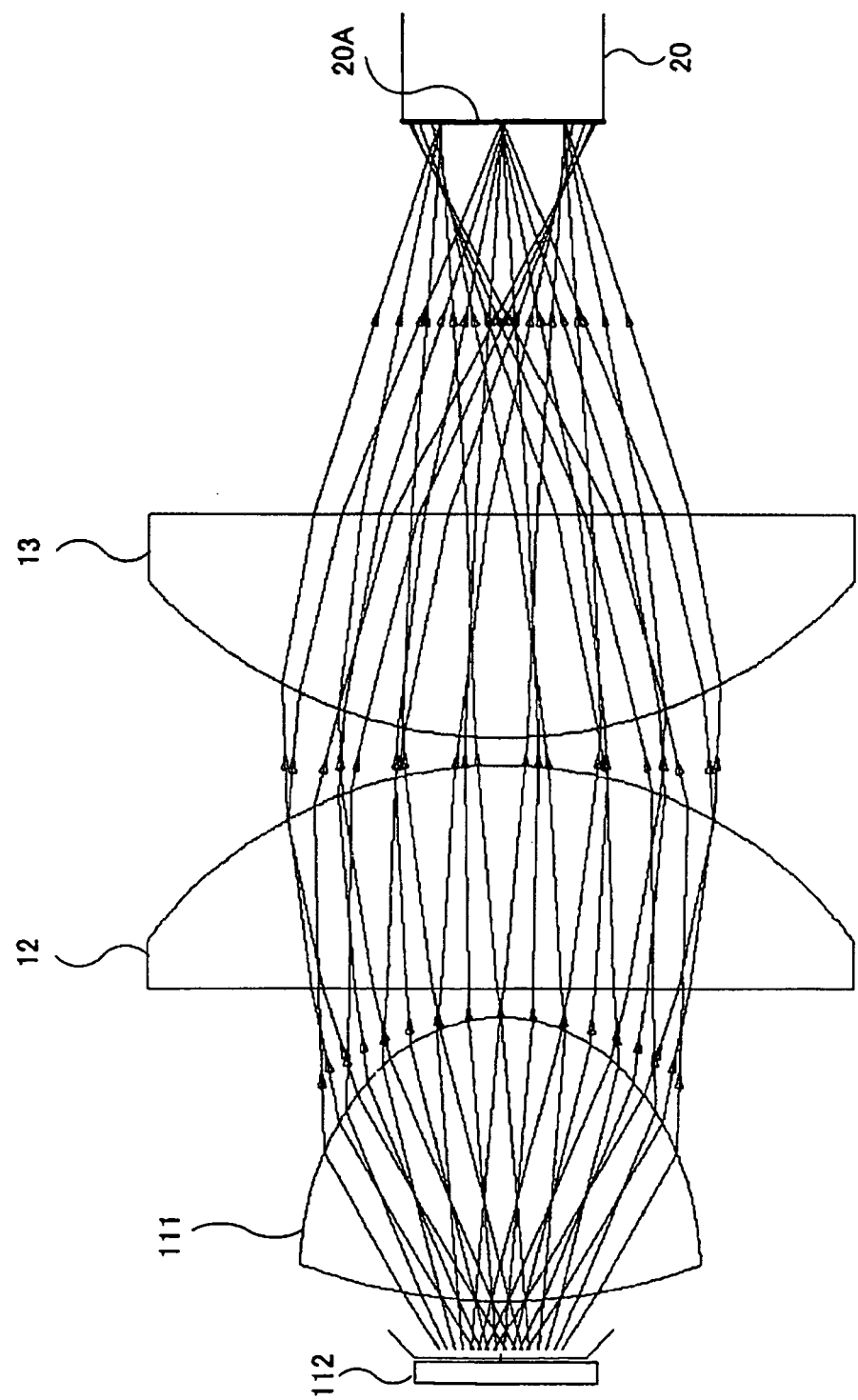
FIG. 2 is an explanatory view showing traces of the light beams of an optical system according to a first mode used for the dental photoirradiation device.

Although there are various modes of the optical system, typical two modes will be described in the embodiment. FIG. 2 is an explanatory view showing traces of the light beams of the optical system according to the first mode. As shown in FIG. 2, the first lens 111 arranged nearest the LED package 112 is the convex lens whose incident and outgoing surfaces have a convex shape. The second lens 12 is the convex lens in which an incident surface has the flat shape while an outgoing surface has the convex shape. In the example, the outgoing surface of the first lens 111 has the aspheric surface and the outgoing surface of the second lens 12 has the spherical surface.

The first lens 111 and the second lens 12 have the function of converting the light beams emitted from the plurality of light-emitting diodes arranged in the LED package 112 into the light beams substantially parallel to the optical axis. The parallel light beams can also be formed only by using the first lens 111. However, in this case, since it is necessary to set the curvatures of the incident surface and the outgoing surface of the first lens 111 to a larger value, the number of light beams internally reflected at the outgoing surface of the first lens 111 is increased and the utilization efficiency is decreased. Therefore, in the embodiment, the internal reflection at the outgoing surface of the first lens 111 is prevented in such a manner that the first lens 111 and the second lens 12 share the refraction of the light beam. Accordingly, the utilization efficiency of the light beam can be significantly increased, and the dental photoirradiation device 100 can be miniaturized and the output of the dental photoirradiation device 100 can be increased.

The third lens 13 is the convex lens in which an incident surface is the spherical surface and an outgoing surface is flat surface. This allows the light beam, which is incident to the third lens 13 and substantially parallel to the optical axis, to be focused on the incident surface 20A of the lightguide 20. At this point, while the LED package 112 is arranged at a position which is slightly inside a primary focus of the optical system (near the first lens 111), the incident surface 20A of the lightguide 20 is arranged at a secondary focus of the optical system. Therefore, the light beam emitted from the light-emitting diode arranged at the position which is far away from the optical axis can be also focused on the incident surface 20A.

Figure 3:
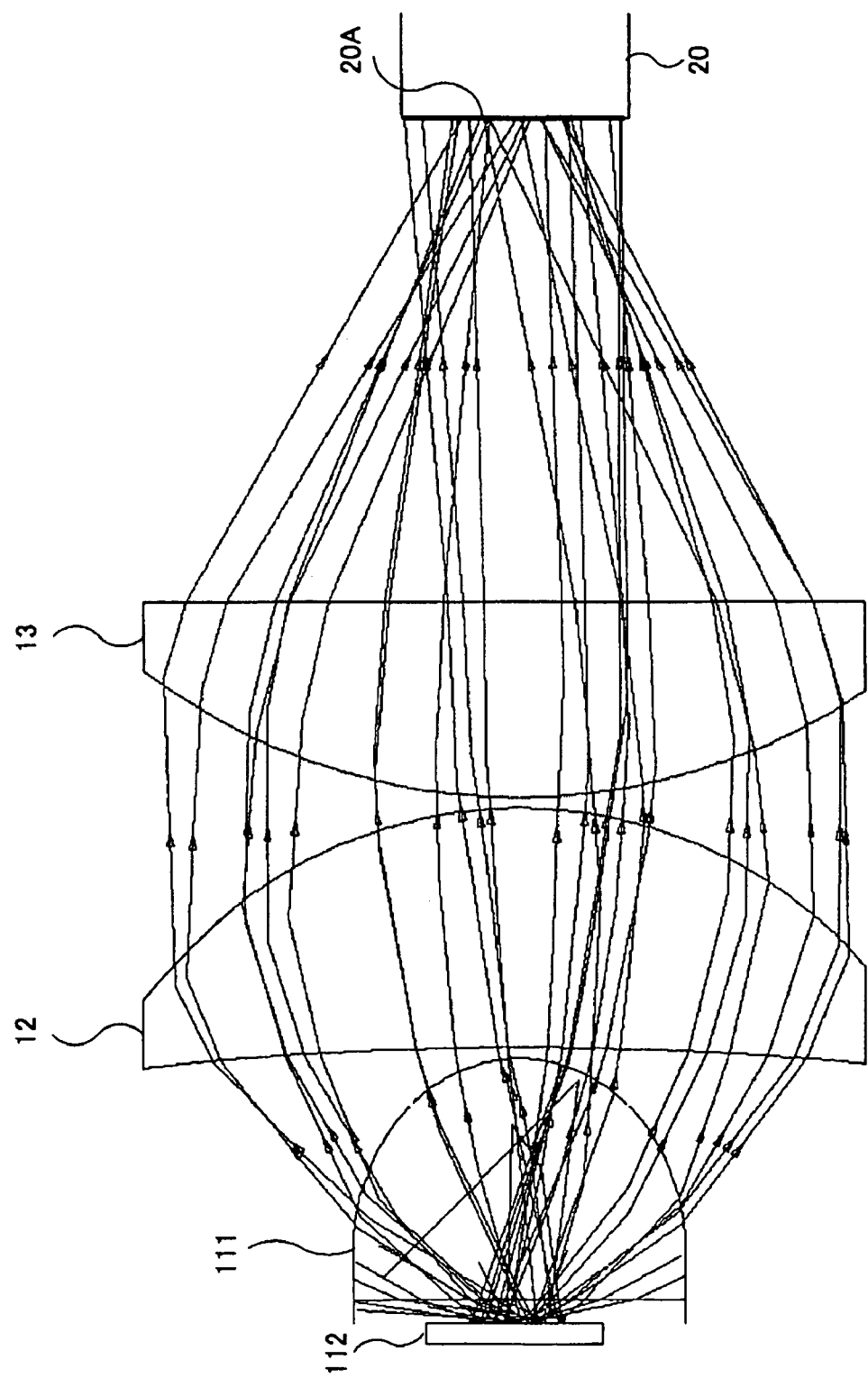
FIG. 3 is an explanatory view showing traces of the light beams of the optical system according to a second mode used for the dental photoirradiation device.

FIG. 3 is an explanatory view showing the traces of the light beams of the optical system according to the second mode. The optical system according to the second mode is similar to the optical system of the first mode shown in FIG. 2 except where the incident surface of the first lens 111 has the flat surface and the incident surface of the second lens 12 has the concave surface. The reason why the incident surface of the first lens 111 has the flat surface is that improvement of productivity is achieved. It is also appreciated that the incident surface of the first lens 111 has the spherical surface, an elliptical surface, or the aspheric surface.

The reason why the incident surface of the second lens 12 has the concave surface is that the spherical aberration is decreased. That is to say, since the outgoing surface of the second lens 12 and the incident surface of the third lens 13 have the spherical surface, the spherical aberration is generated. Among the light beams passing through outer peripheral portions of the second lens 12 and the third lens 13, the number of light beams which do not impinge on the incident surface 20A and the number of light beams whose incident angles exceed an angle at which the light beam can be incident are increased by the spherical aberration. Therefore, the spherical aberration is decreased in such a manner that the incident surface of the second lens 12 is formed in the concave shape. Accordingly, quantity of light incident to the incident surface 20A can be increased and the utilization efficiency of the light beam can be increased.

Figure 4:
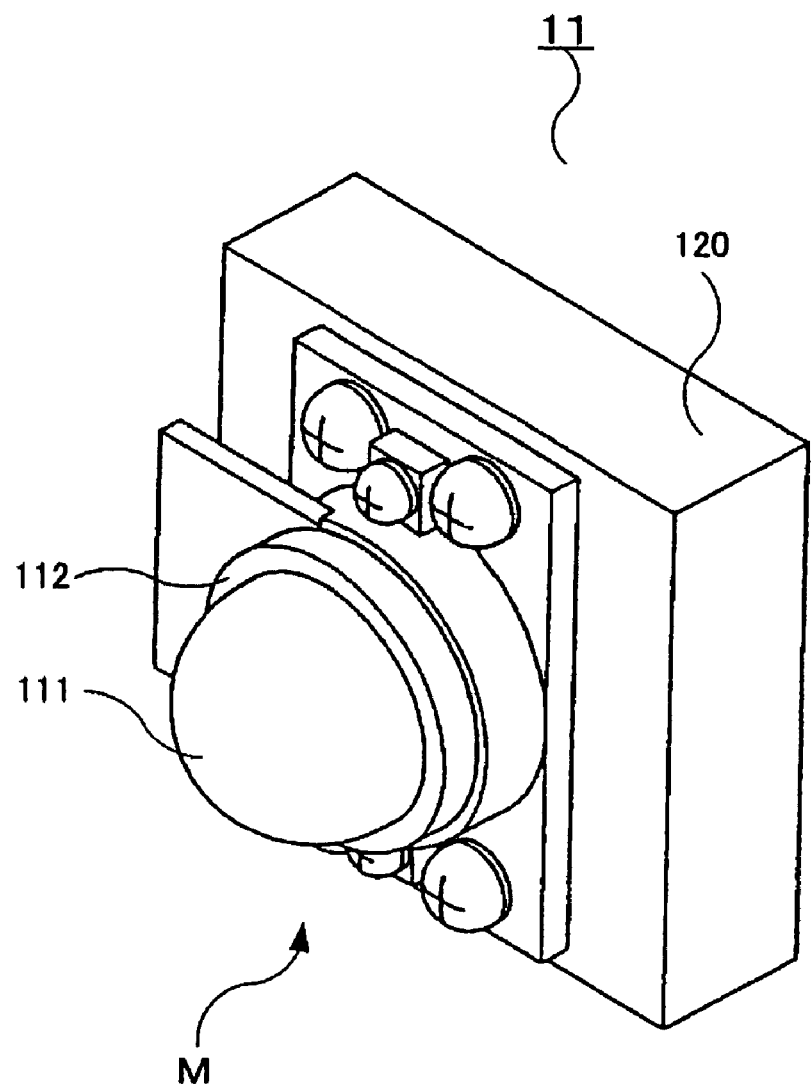
FIG. 4 is a perspective view showing an external appearance of an LED light-emitting unit 11 used for the dental photoirradiation device.
Figure 5:
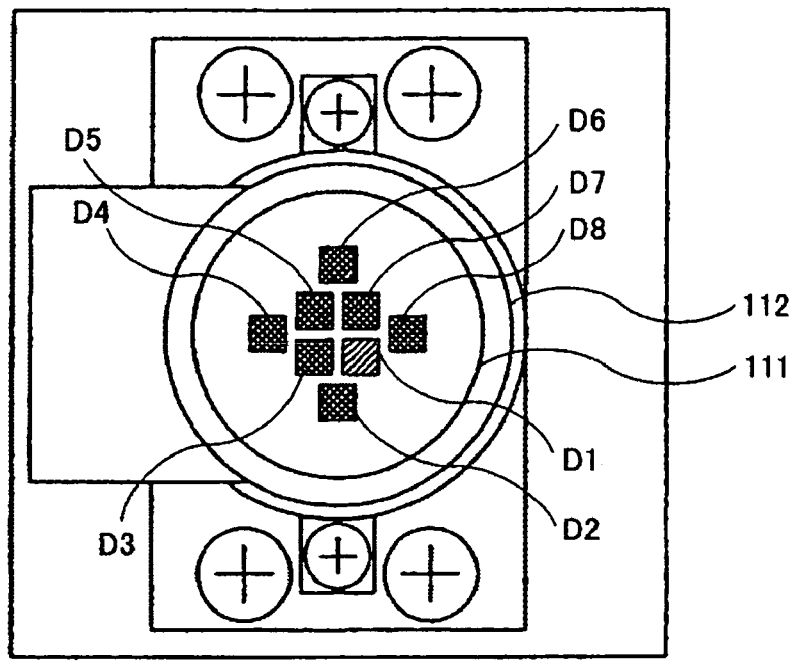
FIG. 5 is a plan view showing the external appearance of an LED light-emitting unit 11 used for the dental photoirradiation device.

Next the LED light-emitting unit 11 will be described. FIG. 4 is a perspective view showing an external appearance of the LED light-emitting unit 11, and FIG. 5 is a plan view of the LED light-emitting unit 11. As shown in FIGS. 4 and 5, the LED light-emitting unit 11 is formed such that an LED module M is screwed on a heat sink 120. The first lens 111 and the LED package 112 are integrally formed in the LED module M.

The LED package 112 includes light-emitting diodes D1 and D2 to D8. While the light-emitting diode D1 has a peak in a light-emitting wavelength ranging from 350 nm to 430 nm, the light-emitting diodes D2 to D8 have the peak in the light-emitting wavelength ranging from 430 nm to 500 nm.

The reason why the light-emitting diodes have two kinds of the peaks of the light-emitting wavelength is as follows: The dental photoirradiation device 100 is used to cure the photo-polymerization resin. In the photo-polymerization resin, two kinds of photo-polymerization catalysts (for example, camphorquinone and acyl phosphine oxide) are contained in monomers. When the photo-polymerization catalyst is irradiated with the light, the photo-polymerization catalyst absorbs the light to generate a radical, and the radical causes the monomer to start the polymerization reaction. However, a wavelength region in which the photo-polymerization occurs depends on the kind of the photo-polymerization catalyst. Therefore, the light-emitting diode shaving the two kinds of the peak wavelengths are used in order to irradiate photo-polymerization catalyst with the light beam having the wavelength according to the kind of the photo-polymerization catalyst. Accordingly, the photo-polymerization reaction can be performed at two steps of pre-curing and complete curing, and the problem that the unpolymerized portion remains can be eliminated by sufficiently curing the photo-polymerization resin.

In the example, the reason why the light-emitting diode D1 is arranged in the center compared with the light-emitting diodes D2, D4, D6, and D8 is that the light beam emitted from the light-emitting diode D1 is located in the center of the irradiation spot. According to the above optical system, the incident light beam near the optical axis is focused near the optical axis. Accordingly, the light beam from the light-emitting diode D1 can be located in the center of the irradiation spot by arranging the light-emitting diode D1 at the position near the center. In the light-emitting diodes D1 to D8, only the light-emitting diode D1 has the light-emitting wavelength different from others. Since the dentist operates the dental photoirradiation device 100 so that the photo-polymerization resin is located in the center of the irradiation spot, the photo-polymerization resin can be securely irradiated with the light beam from the light-emitting diode D1.

(Second Invention)

An embodiment of the second invention will be described below referring to the accompanying drawings. In the embodiment, the dental photoirradiation device for curing the photo-polymerization resin will be described as an example of the photoirradiation device.

Figure 6:
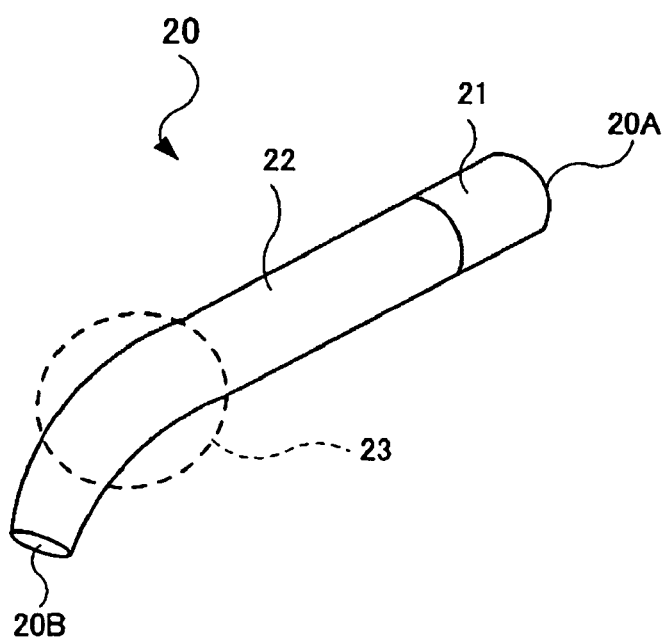
FIG. 6 is a perspective view showing a configuration of the external appearance of a lightguide used for the dental photoirradiation device.
Figure 7:
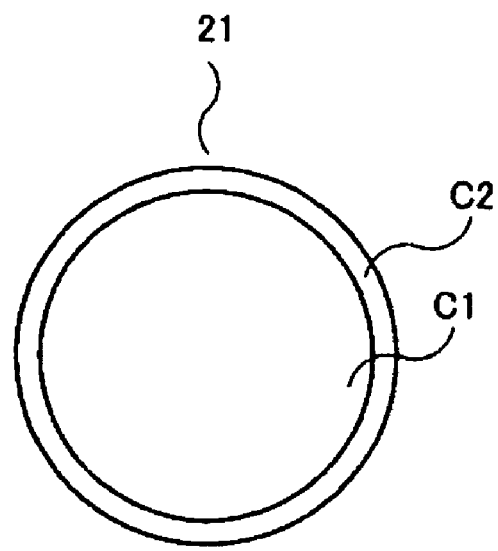
FIG. 7A is a sectional view of a first rod.
FIG. 7B is a sectional view of a second rod.
Figure 7:
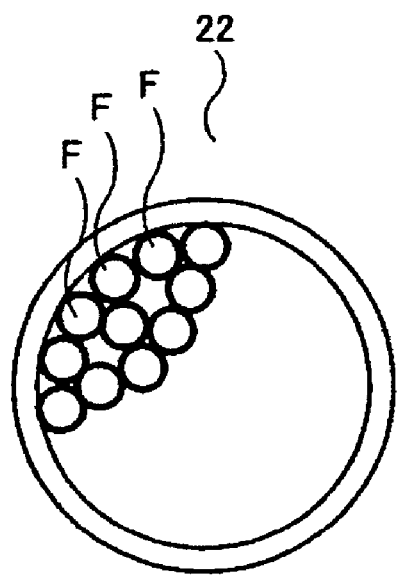
Figure 8:
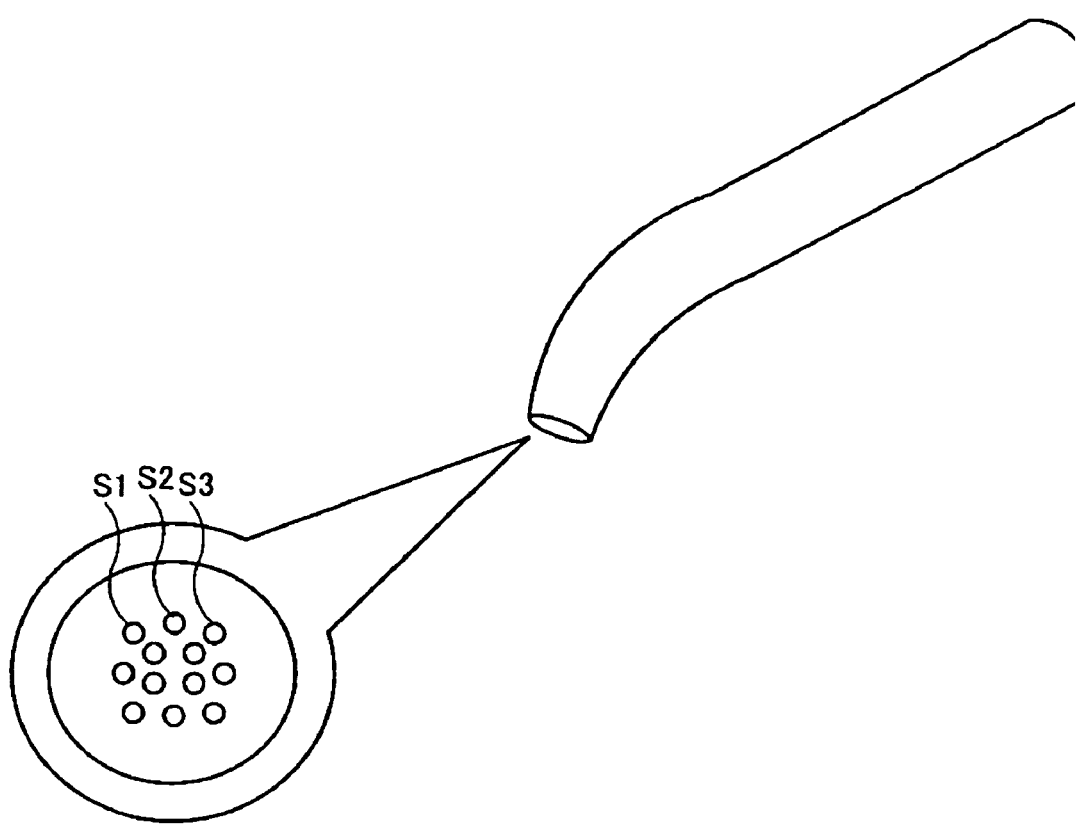
FIG. 8 is an explanatory view for explaining a problem of the conventional lightguide.

FIG. 6 is a perspective view showing the configuration of the external appearance of the lightguide 20. As shown in FIG. 6, the lightguide 20 includes a clad rod type of first rod 21 and a fiber array type of second rod 22 while the clad rod type of first rod 21 and the fiber array type of second rod 22 are connected to each other. FIG. 7A shows a sectional view of the first rod 21, and FIG. 7B shows a sectional view of the second rod 22.

The first rod 21 includes a single fiber. The single fiber includes a core C1 having a high refractive index and a clad C2 having a low refractive index, and the core C1 is coated with the clad C2. In a boundary surface between two transparent material shaving the refractive indexes different from each other, the light beam having the incident angle within a certain angle is completely reflected. The optical fiber guides the light beam by utilizing characteristics of total reflection. The second rod 22 includes the plurality of fibers F with the fibers F bundled. Similarly to the fiber used for the first rod 21, each of the fibers F includes the core C1 and the clad C2, and the core C1 is coated with the clad C2.

Returning to FIG. 6, the lightguide 20 has a bent portion 23 in order to insert the lightguide 20 into the oral cavity of the patient to operate easily. The reason why the bent portion 23 is provided in the second rod 22 is that, in the fiber array type of second rod 22, the increase in damping factor to the curvature is less than that of the clad rod type of first rod 21. Accordingly, the incident light beam can be guided with low damping factor.

In the case where the optical system according to the first mode shown in FIG. 2 is used, since the incident surface 20A of the lightguide 20 is arranged at the secondary focus, an image is focused at the incident surface 20A. The positional relationship among the plurality of light-emitting diodes arranged in the LED package 112 directly affects the image in the form of an inverted image. When the lightguide 20 is formed only by the second rod 22, among the fibers in the second rod 22, the light beams are incident to some fibers and the light beams are not incident to other fibers. This causes the light beams outgoing from the outgoing surface 20B to become the plurality of spot lights.

On the contrary, in the embodiment, since the focused light beams are guided to the second rod 22 through the first rod 21, the light beams are not focused but becomes blurred at a bonded surface between the first rod 21 and the second rod 22. Accordingly, the light beams outgoing from the second rod 22 do not become the plurality of spot lights and brightness becomes uniform.

Even in the case where the optical system according to the second mode shown in FIG. 3 is used, since the focused light beams are guided to the second rod 22 through the first rod 21, the light beams outgoing from the second rod 22 do not become the plurality of spot lights and the brightness becomes uniform.

The invention is not limited to the above-described embodiments. For example, the following modifications can be performed.

(1) The concave lens may be arranged between the optical system and the incident surface 20A of the lightguide 20. In this case, even if the incident surface 20A has a smaller area, the light beams emitted from the light-emitting unit 11 can be focused to the fiber array having a small numerical aperture (NA) while the optical system is small.

(2) The photoirradiation device 100 may be utilized as a spot light source for a UV cured resin or a fiber irradiation device.

(Effect of the Invention)

As described above, according to the first invention, since the first lens and the second lens share the refraction of the light beam in order to obtain the parallel light beams, the internal reflection at the outgoing surface of the first lens can be prevented and the light beams emitted from the plurality of light sources can be efficiently utilized. As a result, the large output can be obtained with the smaller number of point light sources, so that the optical system can be miniaturized, which in turn allows the overall size of the device to be miniaturized.

Further, according to the second invention, the light beams emitted from the plurality of point light sources can be guided with low damping factor and the irradiation light beam can become uniform.

The invention claimed is:

1. A photoirradiation device which outputs a light beam from an outgoing surface of a lightguide unit, the photoirradiation device comprising:
   a plurality of point light sources, each point light source being a light-emitting diode;
   a lightguide unit which has an incident surface and an outgoing surface, the lightguide unit guiding a light beam incident from the incident surface to the outgoing surface; and
   an optical system which focuses the light beams emitted from the plurality of point light sources on the incident surface of the lightguide unit, wherein the plurality of point light sources are arranged on a surface perpendicular to an optical axis of the optical system, the optical system has a first lens, a second lens, and a third lens, which are arranged in order from the point light sources toward the incident surface of the lightguide unit, an incident surface and an outgoing surfaces in the first lens and the second lens are respectively formed so that a light beam emitted from the point light source arranged near the optical axis is diffused from the optical axis by the first lens and the light beam diffused from the optical axis by the first lens is converted into the light beam substantially parallel to the optical axis, and an incident surface and an outgoing surface of the third lens are formed so that the light beams outgoing from the second lens are focused on the incident surface of the lightguide unit.

2. The photoirradiation device according to claim 1, wherein the incident surface of the first lens has a flat surface or a convex surface, and the outgoing surface of the first lens has a convex surface.

3. The photoirradiation device according to claim 1, wherein the incident surface of the second lens has a flat surface or a concave surface, and the outgoing surface of the second lens has a convex surface.

4. The photoirradiation device according to claim 1, wherein the incident surface of the third lens has a convex surface, and the outgoing surface of the third lens has a flat surface.

5. The photoirradiation device according to claim 1, wherein the plurality pf point light sources are arranged at a position which is inside a primary focus of the optical system, and the incident surface of the lightguide unit is arranged at a secondary focus of the optical system.

6. The photoirradiation device according to claim 1, wherein the lightguide unit is a fiber rod which guides a light beam incident to an incident surface to output the light beam from an outgoing surface by using a fiber including a high-refractive index core and low-refractive index clad, the high-refractive index core being coated with the low-refractive index clad, the fiber rod comprising:

a first rod which has a single fiber whose one end becomes the incident surface; and a second rod which has the plurality of fibers, the second rod raking the light beam outgoing from another end of the first rod from one end of the second rod and outputting the light beam from the other end which becomes the outgoing surface.

7. A method of curing a photo-polymerization resin, characterized by using the photoirradiation device according to claim 1.

* * * * *